United States Patent [19]

Hirschberg et al.

[11] Patent Number: 5,584,865
[45] Date of Patent: Dec. 17, 1996

[54] DEFIBRILLATOR WITH OUTPUT STAGE USING SWITCHING NETWORK AND THREE ELECTRODE

[75] Inventors: Jakub Hirschberg, Taeby; Hans Strandberg, Sundbyberg, both of Sweden

[73] Assignee: Pacesetter AB, Solna, Sweden

[21] Appl. No.: 312,323

[22] Filed: Sep. 26, 1994

[30] Foreign Application Priority Data

Sep. 24, 1993 [SE] Sweden ................................ 9303119

[51] Int. Cl.⁶ ........................................................ A61N 1/39
[52] U.S. Cl. ............................................ 607/5; 607/7
[58] Field of Search ................................ 607/5, 4, 2, 15, 607/37, 7

[56] References Cited

U.S. PATENT DOCUMENTS

| | | | |
|---|---|---|---|
| 5,199,429 | 4/1993 | Kroll et al. | 128/419 |
| 5,265,588 | 11/1993 | Nelson et al. | 607/5 |
| 5,318,591 | 6/1994 | Causey, III et al. | 607/5 |
| 5,342,400 | 8/1994 | Hirschberg et al. | 607/5 |
| 5,350,403 | 9/1994 | Stroetmann et al. | 607/5 |
| 5,366,485 | 11/1994 | Kroll et al. | 607/5 |
| 5,376,105 | 12/1994 | Hedberg | 607/5 |
| 5,385,575 | 1/1995 | Adams | 607/5 |
| 5,397,336 | 3/1995 | Hirschberg et al. | 607/5 |
| 5,411,525 | 5/1995 | Swanson et al. | 607/5 |
| 5,411,528 | 5/1995 | Miller et al. | 607/37 |
| 5,468,254 | 11/1995 | Hahn et al. | 607/5 |
| 5,507,781 | 4/1996 | Kroll et al. | 607/5 |

FOREIGN PATENT DOCUMENTS 0280526  8/1988  European Pat. Off. .................. 607/5

*Primary Examiner*—William E. Kamm
*Assistant Examiner*—Carl H. Layno
*Attorney, Agent, or Firm*—Hill, Steadman & Simpson

[57] ABSTRACT

A defibrillator has a pulse-generating device with at least three outputs to which electrodes are connectable for delivering defibrillation pulses. A switching network is provided to reverse the polarity and/or to switch the voltages applied by the pulse-generating device, selectively and at predetermined times, among the electrodes.

21 Claims, 7 Drawing Sheets

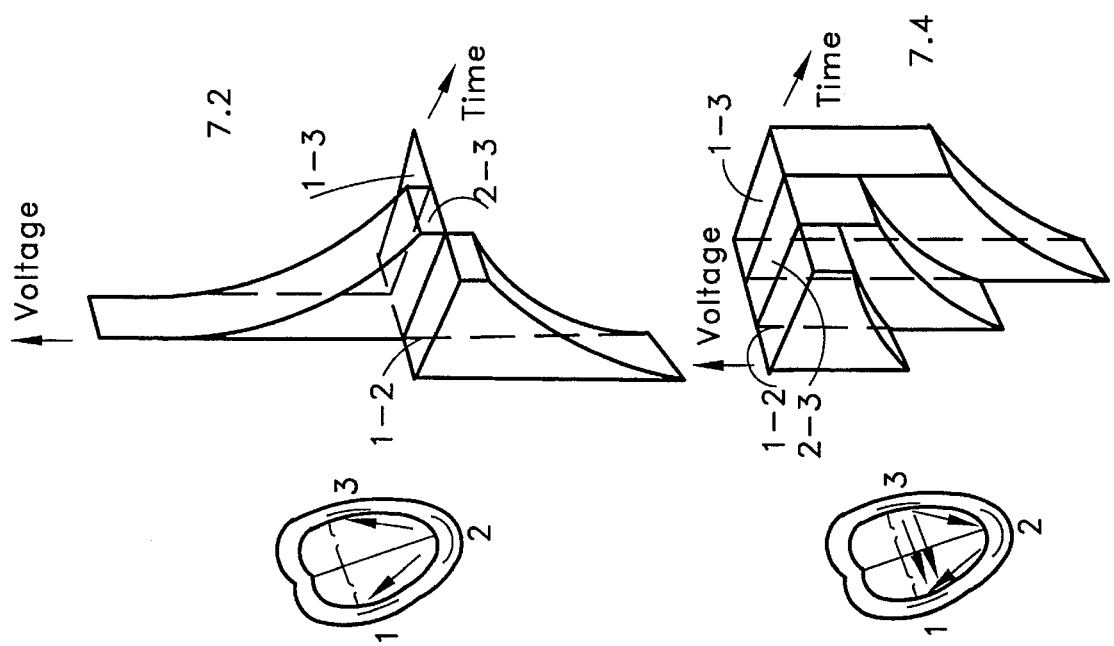
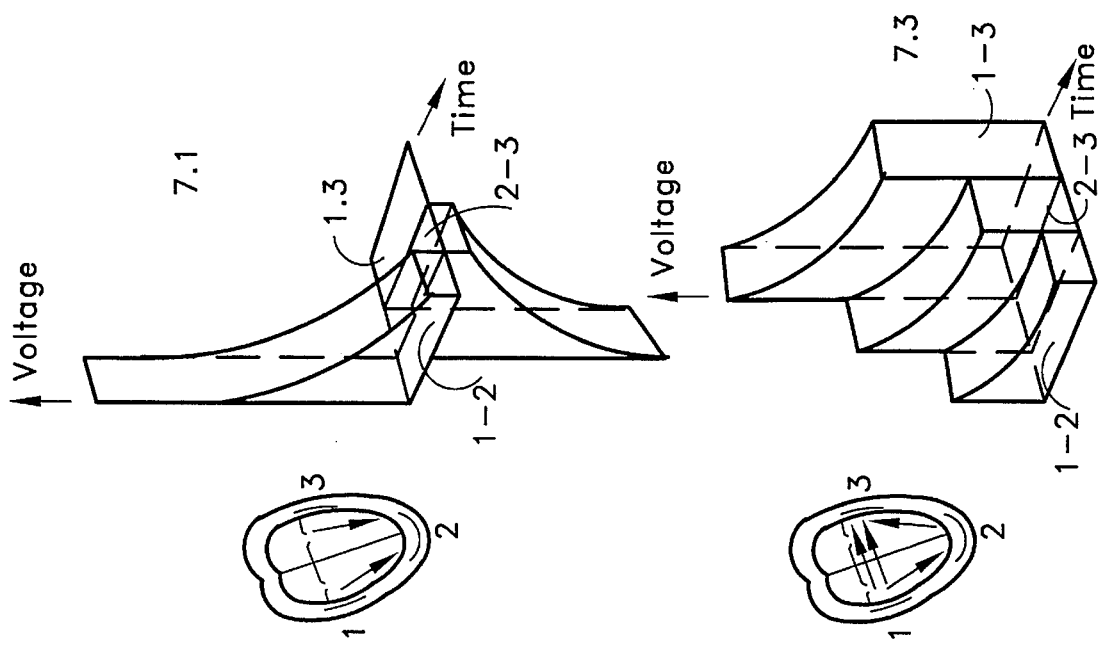
FIG.7

DEFIBRILLATOR WITH OUTPUT STAGE USING SWITCHING NETWORK AND THREE ELECTRODE

BACKGROUND OF THE INVENTION

1. Field of the Invention

The present invention relates to a defibrillator of the type having a pulse-generating device with at least three outputs to which electrodes are connectable for delivering defibrillation pulses.

2. Description of the Prior Art

A defibrillator of this general type is known from German OS 41 10 402. In this known device, electrical impulses are simultaneously emitted across all electrodes, and pulse voltages can be set so there is a favorable distribution of current in the heart tissue. In order to limit the current in the event of a short-circuit, inductances are arranged in the pulse-generating discharge circuit, and the electrodes are supplied with biphasic pulses of current in the form of heavily damped oscillations.

A similar defibrillator is described in published European patent application 0574609. Electrodes, applied at different sites on the heart, are supplied with pulses with different starting times, pulse durations and/or pulse amplitudes, so the most favorable possible distribution of current is achieved in heart tissue.

SUMMARY OF THE INVENTION

An object of the present invention is to provide a defibrillator which achieves both chronologically and spatially optimum distribution of current for heart defibrillation by adaptation to the geometry of the heart.

The above object is achieved in accordance with the principles of the present invention in a defibrillator having a pulse generating device with at least three outputs, to which electrodes are connectable for delivering defibrillation pulses to a heart, with switching means being provided to reverse the polarity of and/or to switch the voltages supplied by the pulse-generating device, the polarity reversal and/or switching taking place selectively and at predetermined times among the electrodes.

In the defibrillator according to the invention, active switching of the voltages in a pulse complex for heart defibrillation is thus performed during the discharge pulses, whereby generation of a plurality of multiphasic pulses of varying intensity, delivered to heart tissue via the electrodes arrayed in the most favorable spatial pattern, becomes possible. The defibrillator according to the invention thus utilizes the lower defibrillation thresholds achieved through the use of at least biphasic pulses combined with the advantages involved in utilizing pulses of varying intensity at different electrodes. In this way, peak voltages and peak currents can be reduced, thereby reducing the risk of damage to tissue. It should also be noted that the polarity of the entire pulse complex need not be changed in order to achieve multiphasic pulses according to the invention; reversal can be limited to just parts of the complex.

It should also be noted that the defibrillator according to the invention can be easily constructed.

In an embodiment of the defibrillator according to the invention, the pulse-generating device contains at least two capacitors, connected in series, which can be charged to the same or different voltages. The switching means can contain a network of controllable switches, devised so all capacitor connections are connectable, in a selectable manner, to any electrode. This maximizes the possibility to vary the intensity and polarity of pulses chronologically and spatially.

DESCRIPTION OF THE DRAWINGS

FIGS. 6–7 show other examples of pulse complexes achieved with the defibrillator according to the invention, associated voltages in the heart being schematically illustrated.

DESCRIPTION OF THE PREFERRED EMBODIMENTS

Figure 1:
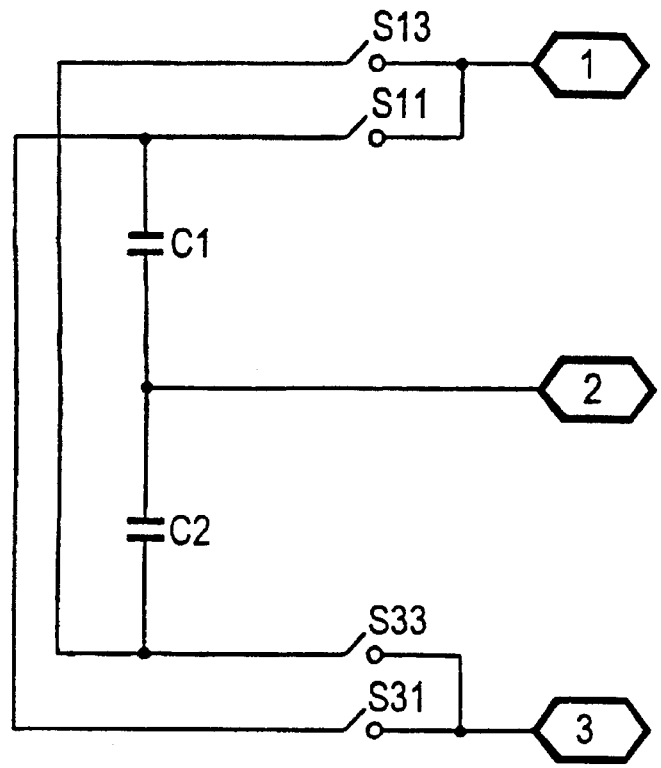
FIGS. 1–3 respectively show the capacitors of the pulse-generating device in the defibrillator or of the invention connected to three electrodes via a network of switches in three different versions.

FIG. 1 shows three electrodes 1, 2 and 3, connected to the terminals on two capacitors C1 and C2 of a pulse-generating device of the defibrillator according to the invention via a first version of a network of switches S11, S13, S31 and S33. The following combinations of voltages between the electrodes 1, 2, 3 can be achieved with this switching network.

Capacitor C2 is connected between electrodes 2 and 1 (the positive electrode is stated first) when switch S13 is closed (conducting), capacitor C1 is connected between electrodes 1 and 2 when switch S11 is closed, capacitor C2 is connected between electrodes 2 and 3 when switch S33 is closed, capacitor C1 is connected between electrodes 3 and 2 when switch S31 is closed, capacitor C1 is connected between electrodes 1 and 2 and capacitor C2 between electrodes 2 and 3 when switches S11 and S33 are closed, capacitor C1 is connected between electrodes 3 and 2 and capacitor C2 between electrodes 2 and 1 when switches S13 and S31 are closed, the electrodes 1 and 3 are interconnected and capacitor C1 is connected between these electrodes 1 and 3 and electrode 2 when switches S11 and S31 are closed, the electrodes 1 and 3 are again interconnected and capacitor C2 is connected between electrode 2 and the interconnected electrodes 1 and 3 when switches S13 and S33 are closed.

Figure 5:
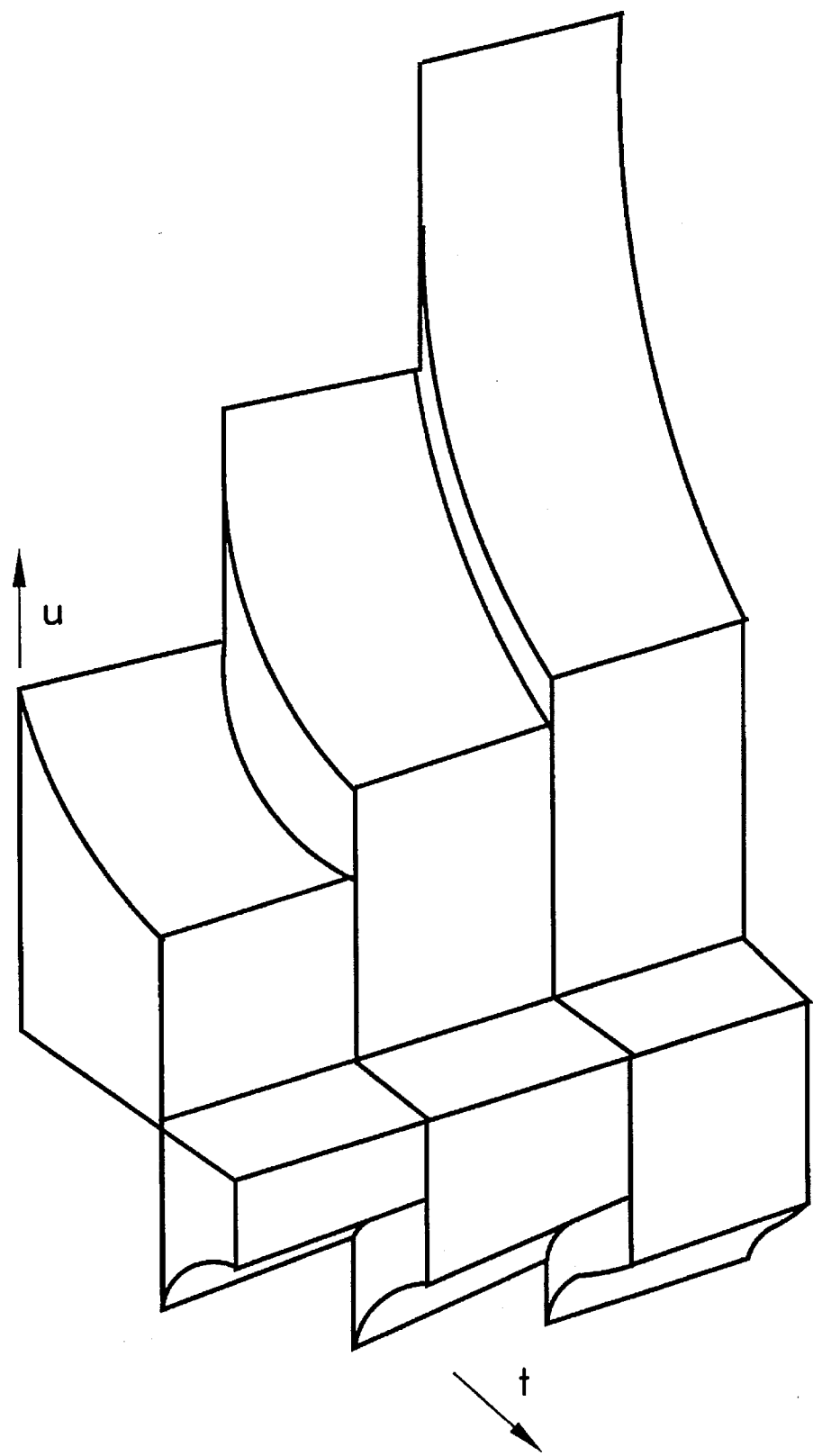
FIG. 5 shows an example of a pulse complex for heart defibrillation realized with the defibrillator according to the invention.

With this simple switching network, a pulse complex with three potential differences can thus be delivered as multiphasic pulses in a three-electrode system. One example of such a pulse complex is shown in FIG. 5. It should be noted that reversal of the polarities of all the voltages in the complex is not necessary. Polarity reversal can be limited only to some of the voltages in the complex.

The switching network can, for example, be switched as follows:

Phase 1: Switches S11 and S33 are closed, electrode 1 then being positive in relation to electrode 2 and electrode 2 being 20 positive in relation to electrode 3. This situation is depicted in FIG. 7.3.

Phase 2: Switch S11 remains closed, switch S33 opens and switch S31 closes, electrode 1 then being positive in relation to electrode 2 and electrode 2 being negative in relation to electrode 3. This situation is depicted in FIG. 7.1.

Phase 3: Switch S13 closes, switch S11 opens and switch S31 closes, electrode 1 then being negative in relation to electrode 2 and electrode 2 being negative in relation to electrode 3. This is the situation depicted in FIG. 7.4.

Figure 2:
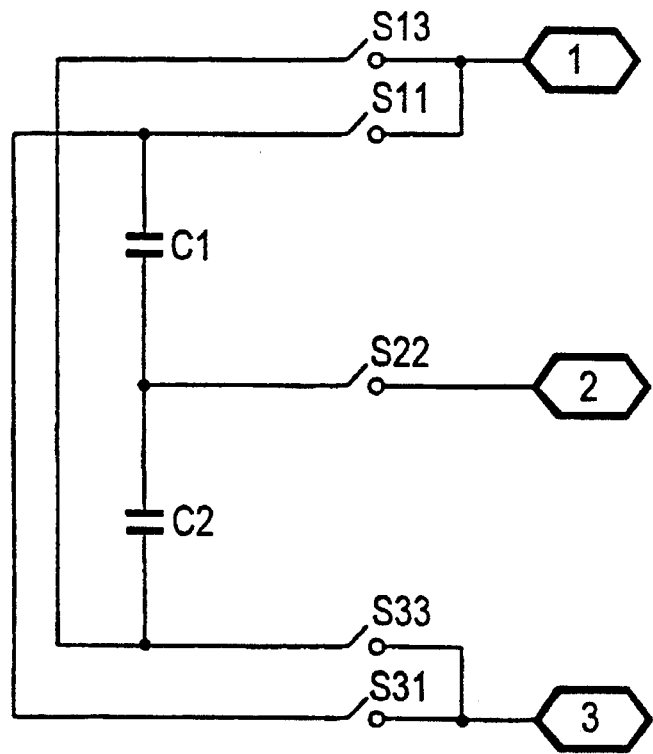

FIG. 2 shows an alternative version of the switching network in which the electrode 2 is connected to the junction point between the capacitors C1 and C2 via an additional switch S22, which further increases the flexibility and makes additional variations of the pulse complex possible.

Figure 3:
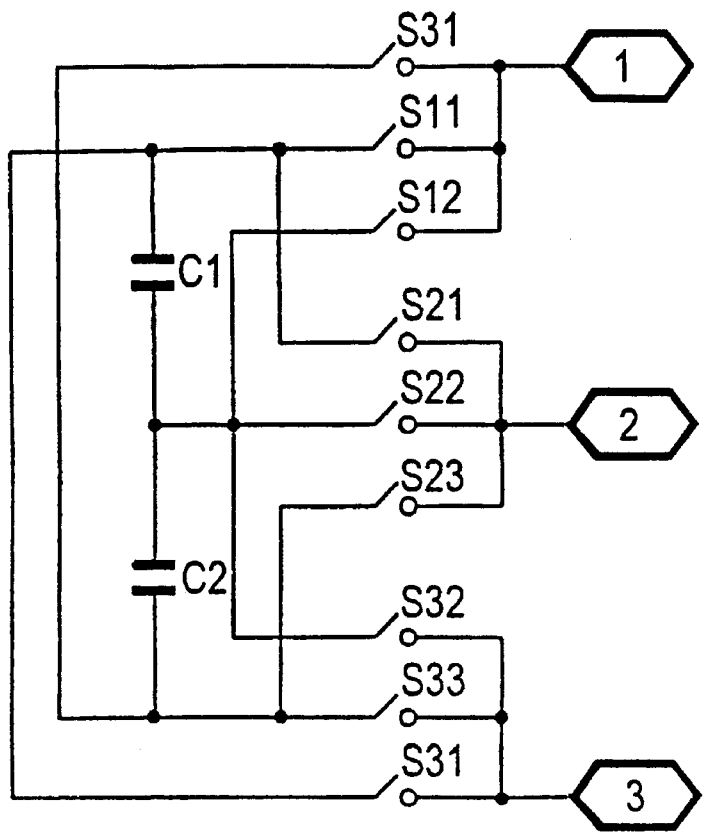

FIG. 3 shows a further embodiment of a switching network which permits optional connection of all capacitor terminals to any of the electrodes 1, 2 and 3. The switching network is devised such that only one of the switches in each group S11, S12, S13 and S21, S22, S23 and S31, S32, S33 can be closed. With this switching network, maximum flexibility is achieved in the ability to vary voltages in a pulse complex.

Once their function is described, devices required for controlling the switching network's switches will be constructable by a person of ordinary skill in the art and therefore such devices have not been shown nor described here.

Figure 4:
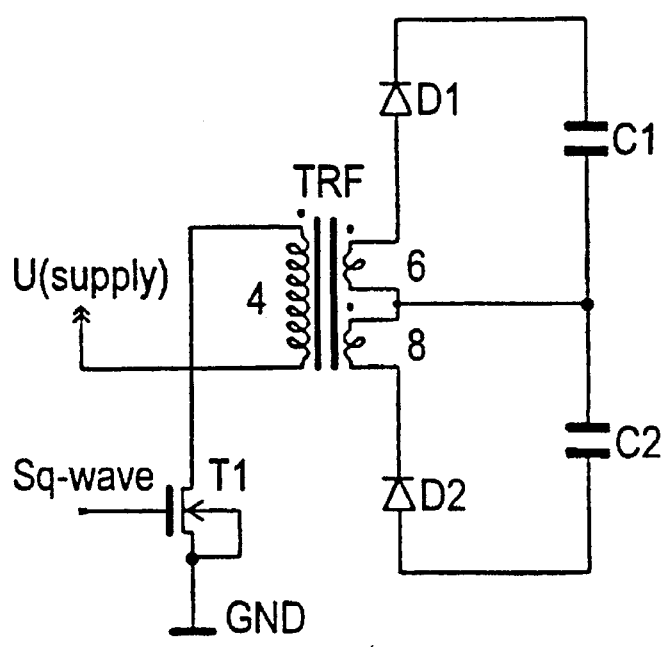
FIG. 4 shows an exemplary embodiment of a charging network for charging the capacitors in FIGS. 1–3.

FIG. 4 shows a circuit diagram for a charging network for charging the discharge capacitors C1 and C2 in the pulse-generating device.

The primary winding 4 of the transformer TRF is connected in series to a switching transistor T1, and the primary winding 4 is supplied with a battery voltage or a stabilized voltage from the battery U(supply). A square wave Sq-wave is chronologically controlled so the transistor TRF becomes exactly saturated when the wave is fed to the transistor gate.

When conduction through the transistor T1 is interrupted, a high voltage develops on the secondary side of the transformer's TRF, formed by sub-windings 6 and 8, so-called flyback transmission.

The secondary winding is subdivided into two sub-windings 6 and 8 to which the discharge capacitors C1 and C2 are respectively connected via diodes D1 and D2.

When the transistor T1 is switched off (non-conducting), the respective voltage pulses in the sub-windings 6 and 8 charge the high-voltage capacitors C1 and C2. The sub-windings 6 and 8 can have the same number of turns, so the capacitors C1 and C2 are charged to the same voltage, or the turns of the sub-windings 6 and 8 can differ in a given ratio so the capacitors C1 and C2 are charged to different voltages.

Charging of the capacitors C1 and C2 is performed with a large number of pulses with a frequency of the order of 10–100 kHz. Charging terminates when the capacitors C1 and C2 attain predetermined voltages.

Devices required for generating the control signal for the switching transistor, as well as the means for measuring capacitor voltages, are not shown in FIG. 4, since they will be apparent to the a person of ordinary skill in the art and do not constitute any part of the present invention.

As noted above, FIG. 5 shows a pulse complex from a defibrillator according to the invention with three electrodes. The pulse complex thus consists of three different voltages whose polarity is reversed at a specific point in time during discharge.

Figure 6:
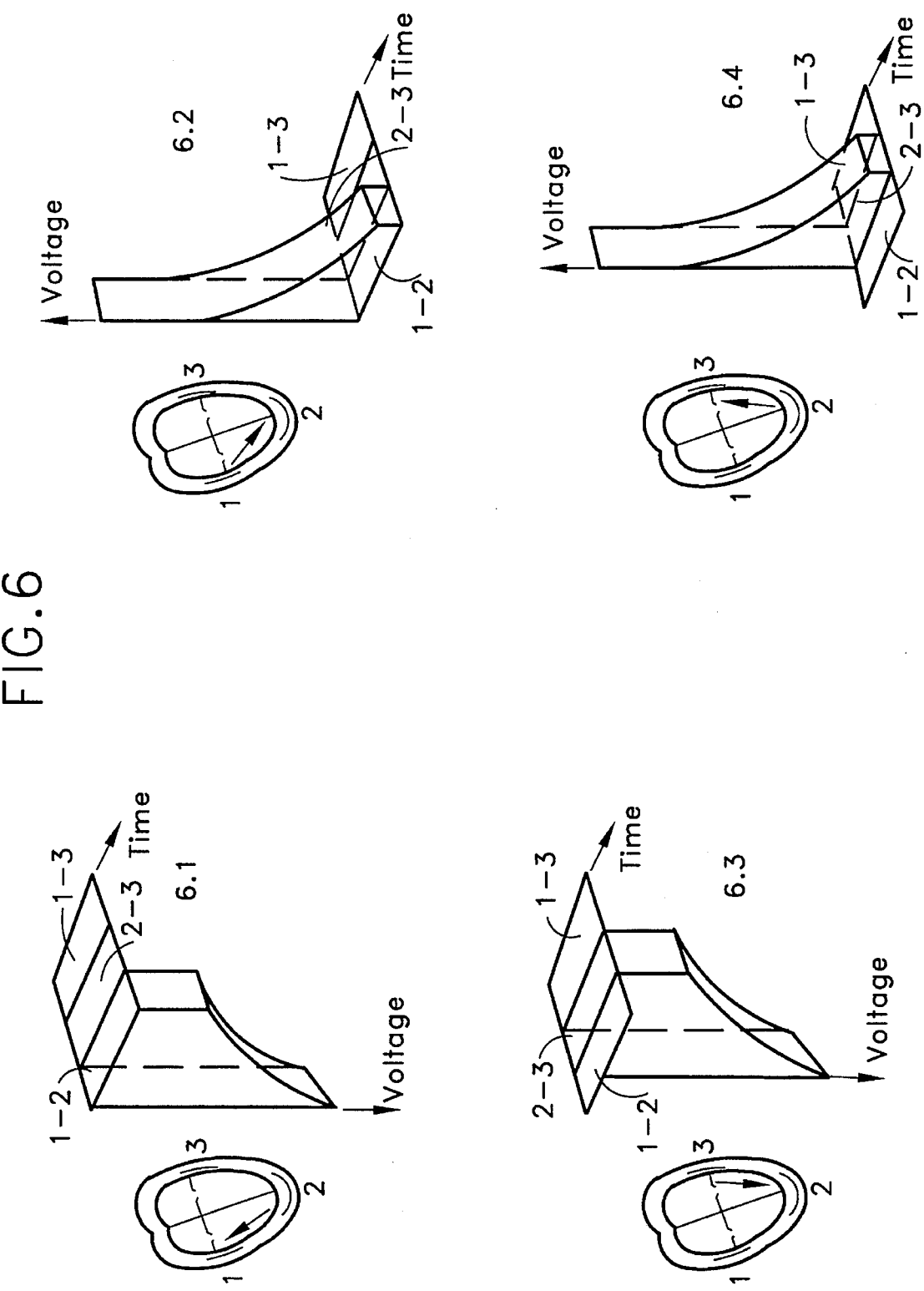

FIG. 6 shows a pulse complex consisting of a single discharge pulse, the polarity of which has been reversed, and which is switched between different pairs of electrodes in a defibrillator according to the invention with three electrodes arranged on a heart, as schematically shown. The corresponding voltage in the heart tissue is schematically illustrated with an arrow, pointing from the positive to the negative electrode, in the heart figure. A reversal of polarity has thus occurred between FIGS. 6.1 and 6.2. Between FIGS. 6.2 and 6.3, there has been a reversal of polarity and a switching of voltage from the electrodes 1–2 to the electrodes 2–3, and yet another reversal of polarity has occurred between FIGS. 6.3 and 6.4.

FIG. 7 shows additional examples of pulse complexes produced by the defibrillator according to the invention. Thus, FIG. 7.1 shows two voltages with opposite polarities arranged between the electrodes 1–2 and 2–3 respectively, and in FIG. 7.2 the pulse complex is shown with reversed polarity. FIG. 7.3 shows a pulse complex with two different voltages, applied between the electrodes 1–2 and 2–3 respectively, with the same polarity and the resulting voltage between the electrodes 1–3. FIG. 7.4 shows the pulse complex with the polarity reversed.

Figure 8:
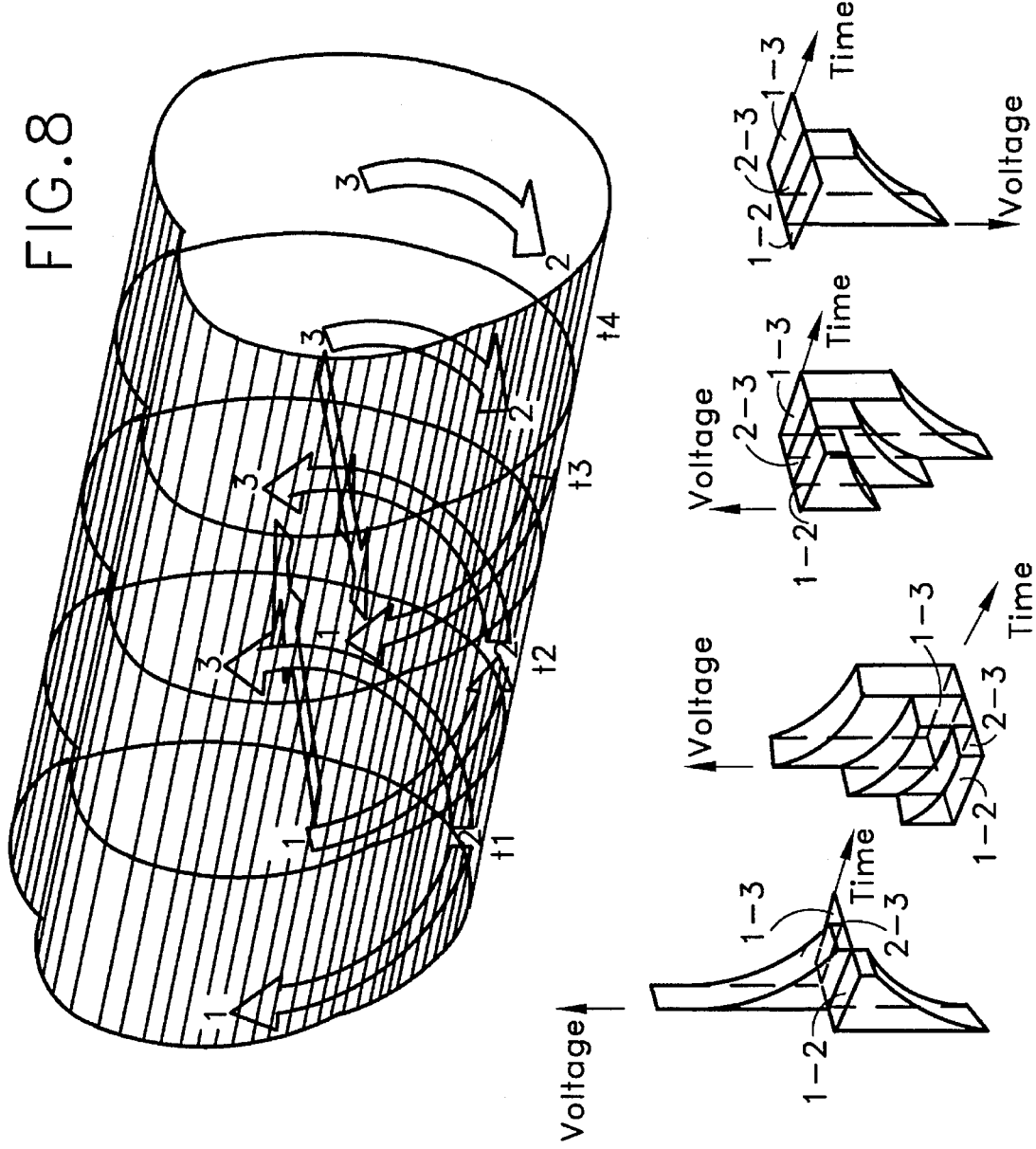
FIG. 8 is an additional illustration of the voltage conditions in the heart with pulse complexes switched in different ways in accordance with the present invention.

FIG. 8 shows a pulse complex, switched at different times t2, t3 and t4, and corresponding voltages in the heart tissue are indicated with arrows in four schematic cross-sections through a heart.

The pulse complex at time t1 corresponds to the complex shown in FIG. 7.1. At time t2 there has been a switch to the complex shown in FIG. 7.3, at time t3 there has been a switch to the complex shown in FIG. 7.4 and at time t4 the pulse complex has been switched to the complex shown in FIG. 6.3.

Figure 9:
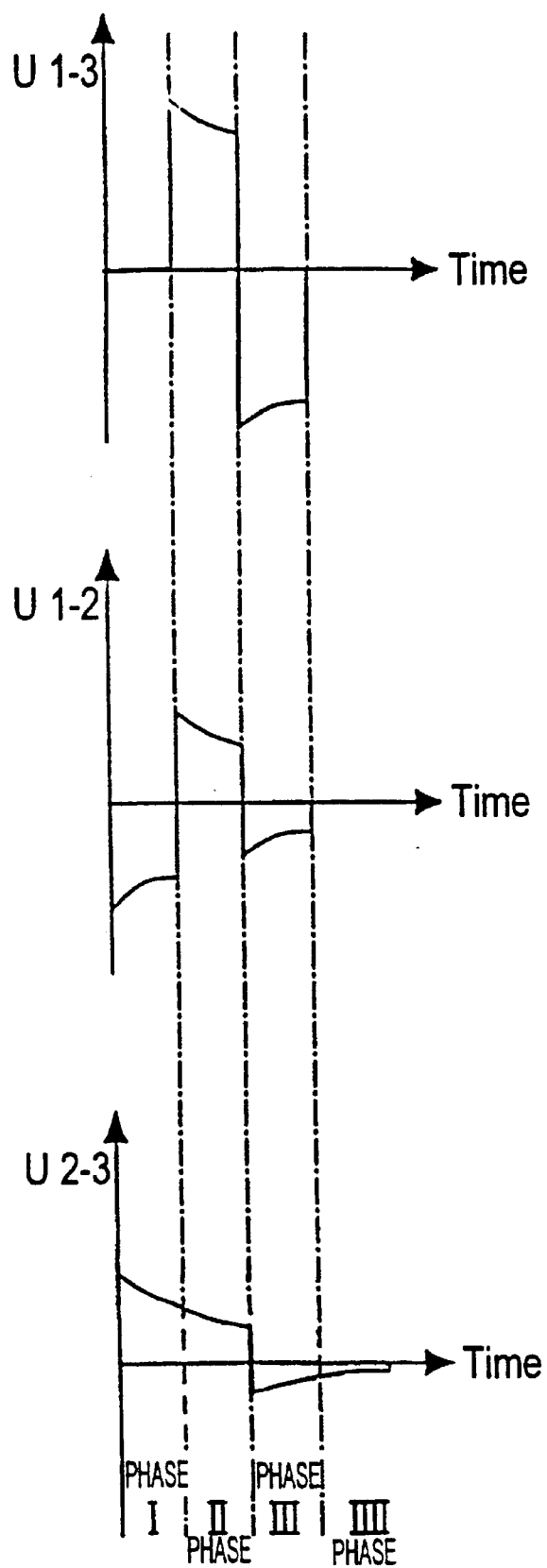
FIG. 9 shows the voltages between the defibrillation electrodes in the example in FIG. 8 with three switchings during a discharge pulse.

FIG. 9 shows the chronological course for the voltages between the different heart electrodes in the situation depicted in FIG. 8. U1–3 designates the voltage between the electrodes 1 and 3, U1–2 is the voltage between the electrodes 1 and 2 and U2–3 is the voltage between the electrodes 2–3.

During the first phase, the voltage between the electrodes 1, and 2 and 2 and 3 are thus of equal magnitude and opposite polarity. The resulting voltage between the electrodes 1 and 3 is then accordingly zero. In the second phase, the polarity of the voltage between the electrodes 1 and 2 has been reversed, and the voltages between these electrodes 1 and 2 and between the electrodes 2 and 3 are added to the illustrated voltage U1–3. In the third phase, the polarity of the voltage between the electrodes 1 and 2 as well as between the electrodes 2 and 3 has been reversed, resulting in the reversed polarity voltage U1–3. In the fourth phase, a negative voltage is applied only between electrodes 2 and 3.

Embodiments of the defibrillator according to the invention have been described above comprising three electrodes and their pulse-generating device including two capacitors. The invention is, however, not limited to the illustrated embodiments. The number of electrodes as well as the number of capacitors, can naturally be increased.

Although modifications and changes may be suggested by those skilled in the art, it is the intention of the inventors to embody within the patent warranted hereon all changes and modifications as reasonably and properly come within the scope of their contribution to the art.

We claim as our invention:

1. A defibrillator comprising:

pulse generator means for generating defibrillation pulses, each having a polarity and a voltage associated therewith, said pulse generator means having at least three outputs and at least two capacitors, each having terminals, for generating said pulses and means for charging said capacitors to respective voltages;

three electrodes adapted for interacting with heart tissue to deliver said pulses from said pulse generator means; and switching means, connecting said electrodes to said outputs, for reversing the polarity of said pulses between said electrodes selectively and at predetermined times, said switching means comprising a network of controllable switches including a plurality of switches arranged so that each of said capacitor terminals is selectively connectable to any of said electrodes through said switching means.

2. A defibrillator as claimed in claim 1 wherein said means for charging said at least two capacitors to respective voltages comprises means for charging said at least two capacitors to the same voltage.

3. A defibrillator as claimed in claim 1 wherein said means for charging said at least two capacitors to respective voltages comprises means for charging said at least two capacitors to different voltages.

4. A defibrillator as claimed in claim 1 wherein said means for charging said at least two capacitors to respective voltages comprises a transformer having a primary winding connected to a power supply and a secondary winding connected to said at least two capacitors.

5. A defibrillator as claimed in claim 4 wherein said secondary winding comprises at least two sub-windings, said at least two capacitors being respectively connected across said at least two sub-windings, and said at least two sub-windings having winding turns in a ratio for charging said at least two capacitors to said respective voltages.

6. A defibrillator as claimed in claim 4 wherein said means for charging said at least two capacitors to respective voltages further comprises a switching transistor connected in series with said primary winding of said transformer and with said power supply, and means for chronologically controlling switching of said switching transistor for exactly saturating said transformer.

7. A defibrillator as claimed in claim 6 wherein said means for chronologically controlling switching of said switching transistor comprises means for supplying a square wave having a frequency in the range of from 10 to 100 kHz to a control electrode of said switching transistor for charging said at least two capacitors over a plurality of periods of said square wave.

8. A defibrillator comprising:

pulse generator means for generating defibrillation pulses, each having a polarity and a voltage associated therewith, said pulse generator means having at least three outputs and at least two capacitors, each having terminals for generating said pulses and means for charging said capacitors to respective voltages;

three electrodes adapted for interacting with heart tissue to deliver said pulses from said pulse generator means; and switching means, connecting said electrodes to said outputs, for switching the voltages of said pulses between said electrodes selectively and at predetermined times, said switching means comprising a network of controllable switches including a plurality of switches arranged so that each of said capacitor terminals is selectively connectable to any of said electrodes through said switching means.

9. A defibrillator as claimed in claim 8 wherein said means for charging said at least two capacitors to respective voltages comprises means for charging said at least two capacitors to the same voltage.

10. A defibrillator as claimed in claim 8 wherein said means for charging said at least two capacitors to respective voltages comprises means for charging said at least two capacitors to different voltages.

11. A defibrillator as claimed in claim 8 wherein said means for charging said at least two capacitors to respective voltages comprises a transformer having a primary winding connected to a power supply and a secondary winding connected to said at least two capacitors.

12. A defibrillator as claimed in claim 11 wherein said secondary winding comprises at least two sub-windings, said at least two capacitors being respectively connected across said at least two sub-windings, and said at least two sub-windings having winding turns in a ratio for charging said at least two capacitors to said respective voltages.

13. A defibrillator as claimed in claim 11 wherein said means for charging said at least two capacitors to respective voltages further comprises a switching transistor connected in series with said primary winding of said transformer and with said power supply, and means for chronologically controlling switching of said switching transistor for exactly saturating said transformer.

14. A defibrillator as claimed in claim 13 wherein said means for chronologically controlling switching of said switching transistor comprises means for supplying a square wave having a frequency in the range of from 10 to 100 kHz to a control electrode of said switching transistor for charging said at least two capacitors over a plurality of periods of said square wave.

15. A defibrillator comprising:

pulse generator means for generating defibrillation pulses, each having a polarity and a voltage associated therewith, said pulse generator means having at least three outputs and at least two capacitors, each having terminals for generating said pulses and means for charging said capacitors to respective voltages;

three electrodes adapted for interacting with heart tissue to deliver said pulses from said pulse generator means; and switching means, connecting said electrodes to said outputs, for reversing the polarity and switching the voltages of said pulses between said electrodes selectively and at predetermined times, said switching means comprising a network of controllable switches including a plurality of switches arranged so that each of said capacitor terminals is selectively connectable to any of said electrodes through said switching means.

16. A defibrillator as claimed in claim 15 wherein said means for charging said at least two capacitors to respective voltages comprises means for charging said at least two capacitors to the same voltage.

17. A defibrillator as claimed in claim 15 wherein said means for charging said at least two capacitors to respective voltages comprises means for charging said at least two capacitors to different voltages.

18. A defibrillator as claimed in claim 15 wherein said means for charging said at least two capacitors to respective voltages comprises a transformer having a primary winding connected to a power supply and a secondary winding connected to said at least two capacitors.

19. A defibrillator as claimed in claim 18 wherein said secondary winding comprises at least two sub-windings, said at least two capacitors being respectively connected across said at least two sub-windings, and said at least two sub-windings having winding turns in a ratio for charging said at least two capacitors to said respective voltages.

20. A defibrillator as claimed in claim 18 wherein said means for charging said at least two capacitors to respective voltages further comprises a switching transistor connected in series with said primary winding of said transformer and with said power supply, and means for chronologically controlling switching of said switching transistor for exactly saturating said transformer.

21. A defibrillator as claimed in claim 20 wherein said means for chronologically controlling switching of said switching transistor comprises means for supplying a square wave having a frequency in the range of from 10 to 100 kHz to a control electrode of said switching transistor for charging said at least two capacitors over a plurality of periods of said square wave.

* * * * *